United States Patent
Richardson

(10) Patent No.: US 9,579,646 B2
(45) Date of Patent: Feb. 28, 2017

(54) DUAL TIP ARRAY DISPENSING HEAD

(71) Applicant: Accel Biotech, Inc., Los Gatos, CA (US)

(72) Inventor: Bruce J. Richardson, Los Gatos, CA (US)

(73) Assignee: ACCEL BIOTECH, INC., Los Gatos, CA (US)

( * ) Notice: Subject to any disclaimer, the term of this patent is extended or adjusted under 35 U.S.C. 154(b) by 0 days.

(21) Appl. No.: 14/808,304

(22) Filed: Jul. 24, 2015

(65) Prior Publication Data

US 2016/0023203 A1 Jan. 28, 2016

Related U.S. Application Data

(60) Provisional application No. 62/028,734, filed on Jul. 24, 2014.

(51) Int. Cl.
*B01L 3/02* (2006.01)
*G01N 35/10* (2006.01)

(52) U.S. Cl.
CPC .......... *B01L 3/0279* (2013.01); *G01N 35/109* (2013.01); *G01N 35/1074* (2013.01); *B01L 2200/023* (2013.01); *Y10S 901/41* (2013.01)

(58) Field of Classification Search
USPC ....................................................... 422/511
See application file for complete search history.

(56) References Cited

U.S. PATENT DOCUMENTS

| | | | |
|---|---|---|---|
| 3,855,868 A | 12/1974 | Sudvaneimi | |
| 4,260,077 A | 4/1981 | Schroeder | |
| 4,830,832 A * | 5/1989 | Arpagaus | B01L 3/0217 422/509 |
| 5,540,889 A | 7/1996 | Gordon et al. | |

(Continued)

*Primary Examiner* — Jill Warden
*Assistant Examiner* — Brittany Fisher
(74) *Attorney, Agent, or Firm* — Thomas Schneck; David M. Schneck

(57) ABSTRACT

An automated multi-function processing head for a laboratory work station having a table for supporting microtiter plates, other fluid receptacles, a movable arm, and a dual tip dispensing head affixed for reciprocal movement along the arm. The workstation combines into a single programmable system the capabilities for automation of a wide range of bioanalytical procedures including sample pipetting, serial dilution, reagent additions, mixing, reaction timing and washing of reaction vessels. The work station is adapted to transfer, dispense and aspirate liquid from one location to another automatically in accordance with user programmed instructions. Fluid is dispensed and aspirated using a dual tip dispensing head having two sets of tip couplers actuated by one drive system. The two sets of tip couplers allow the use of different sizes of pipette tips and tips at different pitches or distances between the centerlines. Integral to the dual tip dispensing head are two arrays of tip couplers that are used to pick up disposable pipette tips, which are automatically picked up by the head and ejected by a tip ejector mechanism. One motor coupled to an actuator is used to control the multiple functions including; tip coupling, fluid aspiration, fluid dispensing, and tip ejection for both arrays of pipette channels. The work station is designed for interactive connection with a remote computer.

4 Claims, 5 Drawing Sheets

(56) References Cited

U.S. PATENT DOCUMENTS

| | | | |
|---|---|---|---|
| 6,399,024 B1* | 6/2002 | Bevirt | B01L 3/0227 422/511 |
| 6,793,891 B2* | 9/2004 | Yiu | B01L 3/022 422/525 |
| 7,189,369 B2* | 3/2007 | Higuchi | B01L 3/0279 422/511 |
| 7,314,598 B2 | 1/2008 | Nishino | |
| 7,673,531 B2 | 3/2010 | May et al. | |
| 7,858,041 B2 | 12/2010 | Muraishi et al. | |
| 8,007,741 B1 | 8/2011 | Heyes | |
| 8,697,012 B2* | 4/2014 | Ikushima | G01N 35/1074 422/509 |
| 2001/0039843 A1* | 11/2001 | Schoeppe | G01N 35/1065 73/863.32 |
| 2005/0220676 A1 | 10/2005 | Tran | |
| 2011/0268627 A1* | 11/2011 | Warhurst | B01L 3/0227 422/511 |
| 2012/0152050 A1 | 6/2012 | Richardson | |
| 2012/0186367 A1 | 7/2012 | D'Amore et al. | |
| 2012/0285298 A1 | 11/2012 | Richardson et al. | |
| 2014/0112839 A1 | 4/2014 | Richardson | |
| 2015/0087078 A1 | 3/2015 | Richardson | |

* cited by examiner

SECTION B-B

DUAL TIP ARRAY DISPENSING HEAD

CROSS REFERENCE TO RELATED APPLICATION

This application claims priority from U.S. Provisional Application Ser. No. 62/028,734; filed Jul. 24, 2014, which is hereby incorporated by reference herein for all purposes.

TECHNICAL FIELD

The technical field of the present disclosure relates to devices and methods for material handling and robotics, and, more particularly, to automated laboratory work stations, tools useful for such work stations and related methods, all related to the performance of chemical, biochemical, and molecular assays and reactions.

BACKGROUND

Automated liquid handling using robotic systems is a technology used for decades in chemical and biochemical fields for reaction preparation and sample processing. Such systems provide a number of advantages, which include high throughput, precision dispensing, labor savings (and attendant cost reduction) and a high degree of repeatability.

One such automated liquid handling system is the Accel-Bot Mini™ sold by AccelBiotech (Los Gatos, Calif.). This device provides a small footprint system, which is easy to install, self-contained, light weight, yet provides capacity for processing multiple plates and high precision. A hinged cover included as part of the housing allows both a side and top to be exposed, allowing access during loading or maintenance and allowing a sealed system during sample processing. The system includes an x axis track onto which is mounted a y axis arm. Onto y axis arm is mounted a dispensing tool, which may move in the z axis. The dispensing tool is an eight channel pipetting tool, which may include a means for washing the pipettes. The system has a high speed, repeatability and precision, utilizing a 2-phase stepper motor with microstepping in the drive system. The system is controlled by an external computer, allowing a variety of teaching methods for programming the robotic system, including manual input and automated selection. The device has an external interface (e.g. a USB interface) to allow input and output of signals. Temperature control is also provided as part of the system.

Such a workstation combines into a single programmable system the capabilities for automation of a wide range of bioanalytical procedures including: sample pipetting, serial dilution, reagent additions, mixing, reaction timing, washing of reaction vessels, and incubation that requires sealing of the reaction vessel. The work station may include components to transfer, dispense, and aspirate liquid from one location to another automatically in accordance with user programmed instructions.

Workstations of the type described will include a dispense tool mounted such that the tool can be moved in an x-y plane. For example, a tool slidable along a y-axis moving arm, the arm mounted on an x-axis rail, would allow the tool to be positioned at x-y coordinates. This would allow the tool to address locations at one or more locations.

The present x-y robots currently may read to dispense different volumes of liquid, and/or may require a dispense tool (e.g., a pipetting device) that allows for varied spacing of dispense tips. The present embodiments address this need.

SUMMARY

A workstation for automated fluid transfer comprising a dual tip array dispensing head is disclosed herein. The workstation comprises a multi-axis robotic system, which itself comprises a dispense head attached to a motorized drive system. The drive may be capable of moving the robotic system along three axes, as well as rotationally. The drive system may be actuated by a single drive motor.

The automated fluid transfer system may be used in a broad range of analytical procedures, including but not limited to pipetting, dilution, and reagent mixing. In one embodiment, the fluid transfer system comprises a multi-channel pipetting tool. The multi-channel pipetting tool further comprises a dual dispensing tip configuration, wherein the dispensing tips have two different volumes.

The multi-channel pipetting tool system may further comprise a 2-phase stepper motor configured to drive a dual piston configuration. The dual piston configuration comprises two sets of pistons having two different sizes, corresponding to the dual dispensing tip configuration of the multi-channel pipetting tool. The pistons are configured to aspirate/dispense fluid through the dual dispensing tips via vertical linear motion of the pistons driven by the stepper motor.

The multi-channel pipetting tool system may further comprise an ejector means coupled to the dual dispensing tip configuration. The ejector means may be actuated by the pistons associated with each tip of the dispense head, driven by the aforementioned stepper motor.

DETAILED DESCRIPTION

The described embodiments may be used with the devices described in U.S. patent application Ser. No. 13/324,640 entitled Three-Axis Robotic System with Linear Bearing Supports; U.S. patent application Ser. No. 13/467,788 entitled Improved Socket Coupling Receptacle; U.S. patent application Ser. No. 14/062,567 Multi-Function Dispense Head; and U.S. Patent Application Ser. No. 61/881,840. All of these references are hereby expressly incorporated by reference for all purposes herein.

Figure 1:
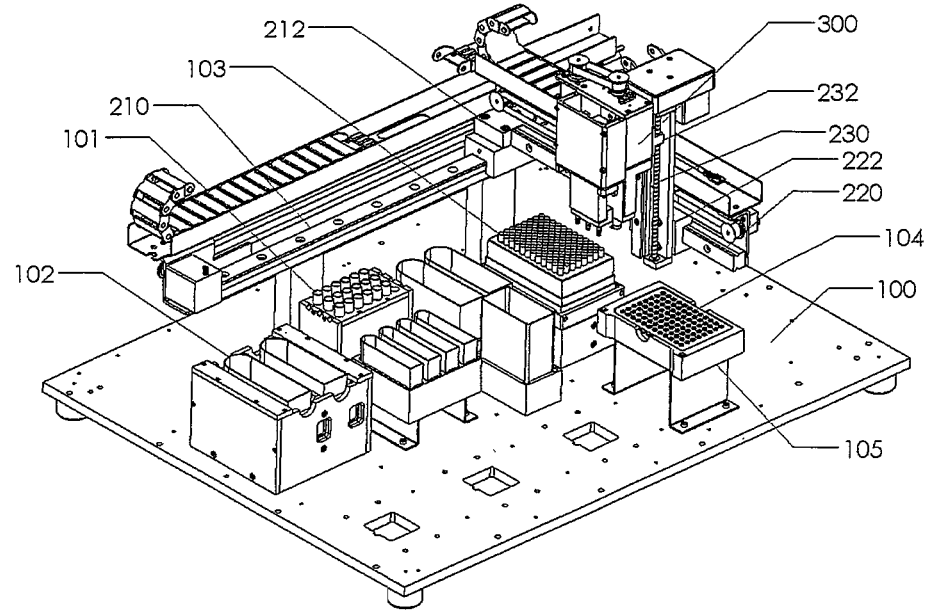
FIG. 1 is a top perspective view of a workstation including a dual tip array dispensing head.

With reference to FIG. 1, the dual tip dispense head 300 is attached to a multi-axis robotic system. The head performs multiple functions including pick up of large and small tips, aspiration and dispensing from large and small tips, and ejection of large and small tips. Aspiration and dispensing as well as tip ejection (for both large and small tips) are all controlled by a single drive screw turned by a single motor. This dual tip dispensing head could be mounted to almost any type of special drive system, an x, y, z, robot 200 (as pictured in FIG. 1), an r theta system (not shown), and/or any other motion system. The head is unique in that only one drive motor is used to perform the multiple functions.

On the work surface 100 are reagent delivery trays 102, large pipette tips 101, small pipette tips 103, and a microtiter plate 104. For the purposes herein "microtiter plate", "microplate" and "multi well plate" are used interchangeably. These plates are the consumables on which this tool will commonly be used. The plates include rows and columns of discrete wells. Common formats include 96 well (8×12 well row/column configuration), but 24, 384 and 1536 sample wells are also commercially available, with the wells arranged in a 2:3 rectangular matrix. Each well of a microplate may hold somewhere between tens of nanoliters (for very high density wells) to several milliliters of liquid. A 96 well plate may hold one cc of liquid. The wells can be any of a number of formats including round wells and square wells. Wells may include a lid (e.g. a sealing silicone cap). Storage of a microplate at low temperatures preserves well contents. Alternatively, the wells can be sealed with a film. The plates are versatile, and can be heated to evaporate volatile liquid or incubate cells with a well. Currently microplates are sold for a myriad of applications, including filtration, separation, optical detection (e.g. using fluorescent stains), storage, reaction mixing, cell culture and cell motility studies, and numerous other uses.

Figure 2:
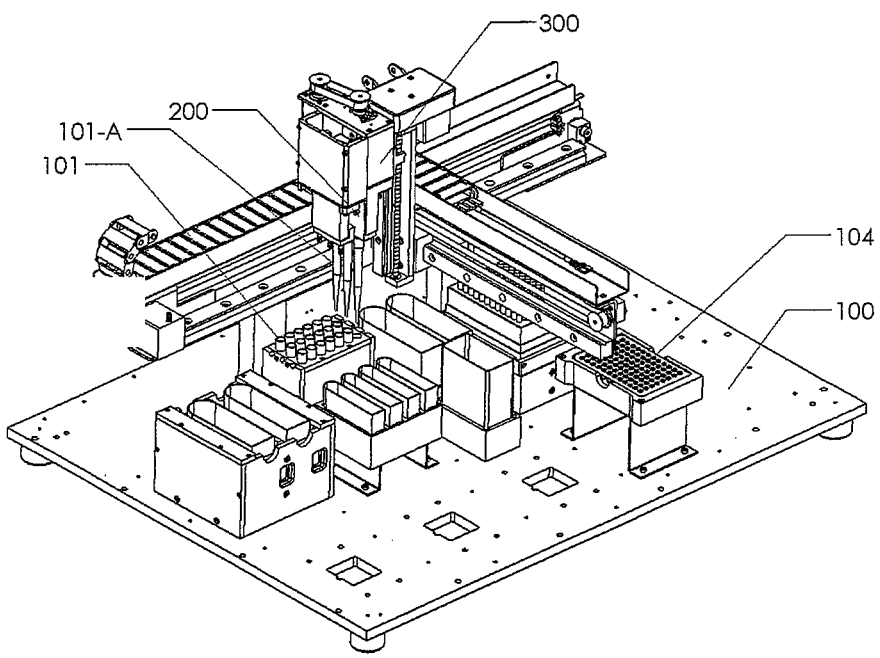
FIG. 2 is the top perspective view of FIG. 1, in which the dual tip array dispensing head has a set of large tips mounted onto the large tip couplers.

The multi-axis robot 200 is used to position the dual tip dispensing head 300 to the different locations on the work surface 100. In FIG. 2, the dual tip dispensing head is shown with tips 101a coupled to the dual tip dispensing head 100.

These pipettes operate by piston-driven air displacement. A pipette tip is sealed onto a tip coupler. This may be a large tip coupler (here "large tip" means having a maximum capacity of at least 1000 μl) or a small tip coupler (here "small tip" means having a capacity of 200 μl or less). When a piston is in an air sealed relation with the tip coupler (and hence the tip) movement of the piston down into the tip coupler will displace a volume of air from the tip. When the piston is retracted from the coupler, a vacuum is created. The piston may be made of metal, ceramic or other material. The seating of the piston is airtight, allowing a controlled volume to be displaced. As the piston is moved upward, a vacuum is formed in the area vacated by the piston. The liquid at the opening of the pipette tip is thus drawn by vacuum force into the pipette tip. The tip can be moved to a transfer location. The piston is then again moved down into the tip coupler, displacing the contents within the tip at a new location.

Such transfer is accurate, repeatable, and can be precise. The use of an automated system increases speed, repeatability, and allows automated programming and tracking of steps. Control of system temperature can add to system precision.

Figure 3A:
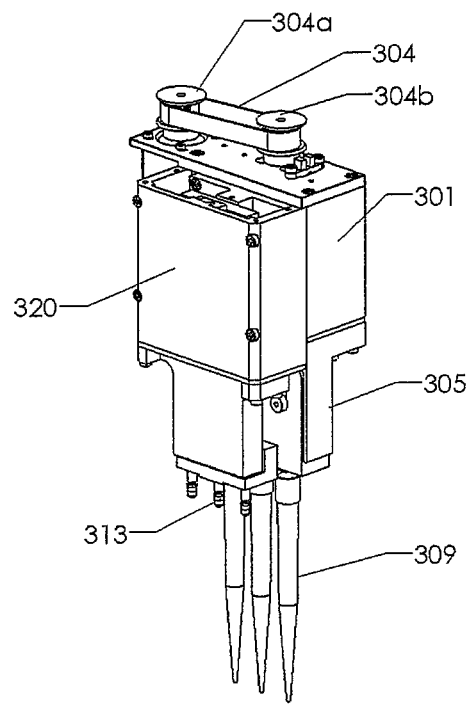
FIG. 3A is a front perspective view of a dual tip array dispensing head with large tips mounted on the large tip couplers.
Figure 3B:
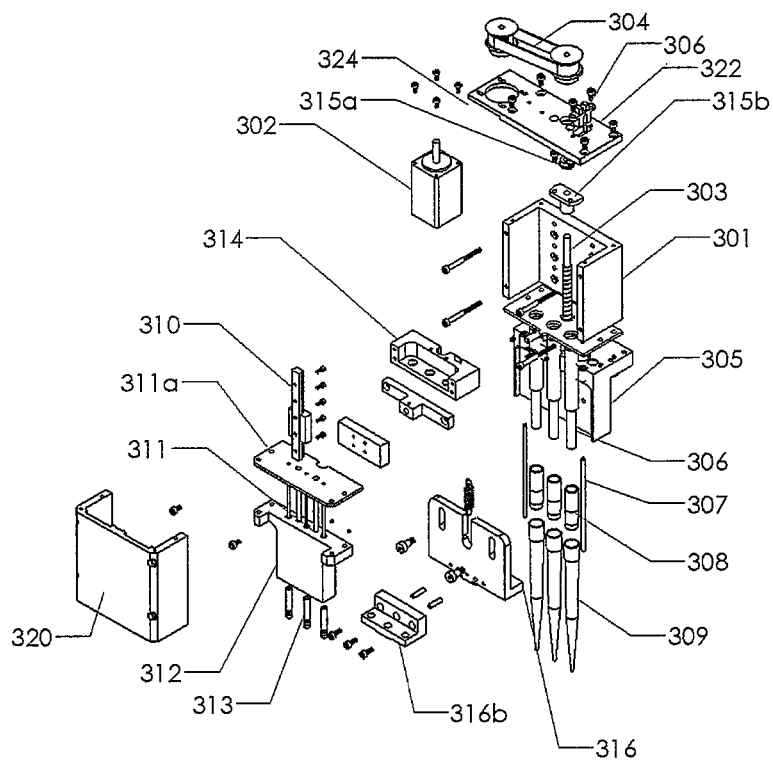
FIG. 3B is an exploded view of the dual tip array dispensing head of FIG. 3A.

With reference to FIGS. 3A, 3B, the dual tip dispensing head 300 includes the following elements: The frame 301 supports most of the elements. The motor 302 is used to drive the pulley 304 that is attached to the leadscrew 303, providing vertical linear motion to drive the large dispense pistons 306 and the small dispense pistons 311. The leadscrew 303 is rotated in the drive nut 315 to provide linear motion. The nut 315 is attached to block 314 which drives rods 307 to move the tip ejector plate 316. The motion provided by the nut 315 is used to drive two sets of pistons used to aspirate and dispense fluids and to facilitate the tip ejection for both sets of tips. The large pistons are sealed in the large piston support housing 305 and the small pistons 311 are sealed and supported in the small support block 312. Attached to the large piston support housing 305 are the large tip couplers 308 and the attached to the small piston support block 312 are the small tip couplers 313. The tip couplers are used to pick up pipette tips and to make a seal. FIG. 3 shows the large tip couplers connected to large pipette tips 309. The small tip couplers 313 couple to small pipette tips (not shown).

The tips 309 are used to aspirate and then dispense fluids. The motor that was used to eject the tips pushes pistons/rods 306 to create a vacuum or pressure that is used to aspirate and dispense fluids in the tips 309. The pistons/rods 306 are sealed at the top of the piston by an o-ring seal. The pistons/rods 306 are driven by block 314 that is attached to a linear bearing 310 and driven by a nut and lead screw 303 via rotation provided by the motor 302.

Figure 4A:
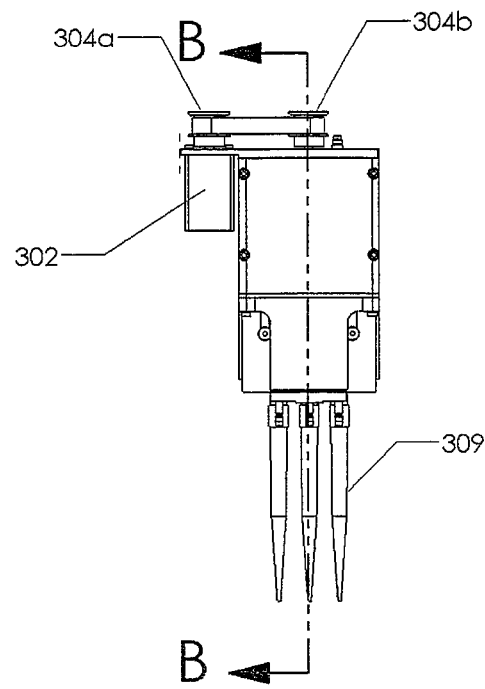
FIG. 4A is a front view of the dual tip array dispensing head.
Figure 4B:
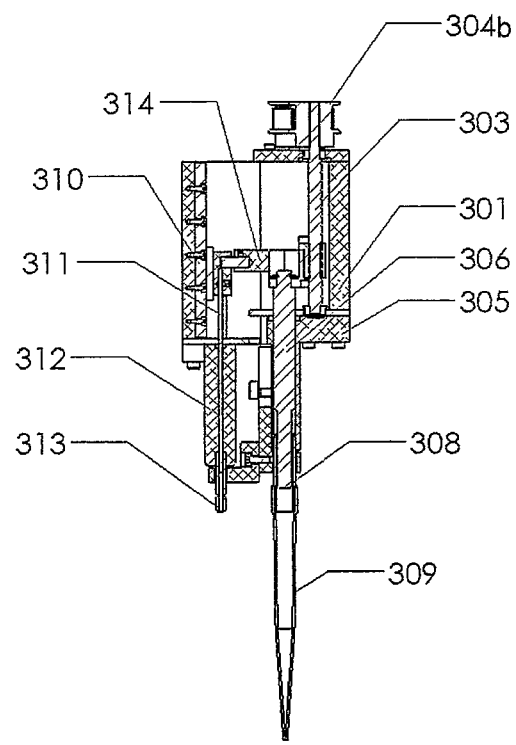
FIG. 4B is a cross section of the dual tip array dispensing head of FIG. 4A.
Figure 4C:
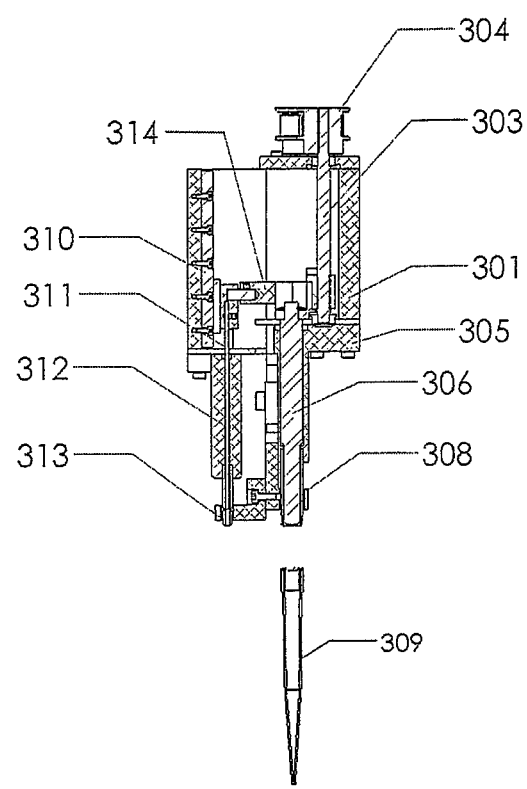
FIG. 4C is the cross section of FIG. 4B with a tip shown removed from the tip coupler, the tip ejection mechanism extended, and the tip displaced from its respective large tip coupler.

With reference to FIGS. 4A-C, the dual tip dispensing head 300 is shown with the piston 306 in the retracted and fully extended positions, respectively. Large pipette tips 309 are depicted coupled to large tip couplers 308 (FIG. 4A and) for aspirating or dispensing larger volumes in an automated fluid transfer system.

FIG. 4A presents a front perspective view of a dual tip dispensing head 300 coupled with large pipette tips 309. When viewed along cross-section B-B in FIG. 4A, block 314 coupled to piston 306 is shown fully retracted in frame 301 in FIG. 4B.

With the piston 306 in the retracted position, as shown in FIG. 4B, the dual tip dispensing head 300 is shown coupled with the large pipette tips 309. In this configuration, vertical linear motion of piston 306 allows for aspiration or dispensing of fluid from pipette tips 309. Small dispense pistons 311 are also in the fully retracted position, with the small tip couplers 313 in a configuration to receive small pipette tips.

In FIG. 4C, a cross sectional view of the dual tip dispensing head 300 is shown detached from large pipette tip 309. In this position, block 314 is at the bottom of leadscrew 303, putting piston 306 in the fully extended position, with the end of the piston 309 extending out of the bottom of large tip coupler 308. In this position, piston 306 has ejected the large pipette tip 309. Small dispense piston 311 is also shown extending out of the bottom of small tip coupler 313. In this position, small pipette tips would be ejected if coupled to small tip coupler 313.

Figure 5:
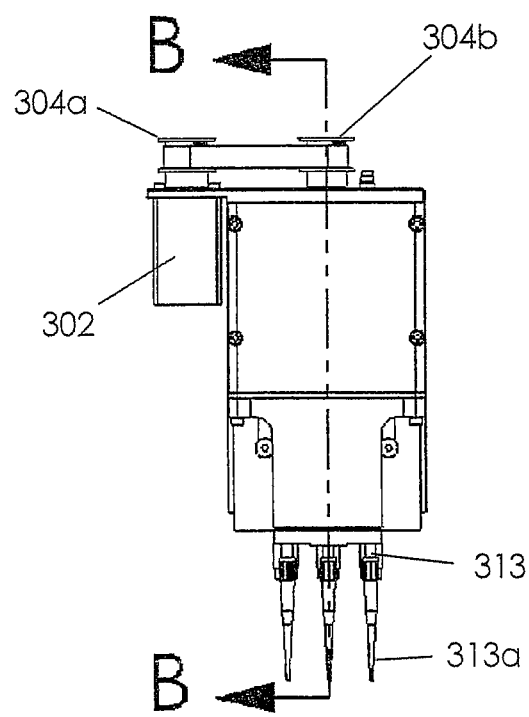
FIG. 5 is a front view of the dispense head with the piston retracted and with small dispense tips attached.
Figure 5A:
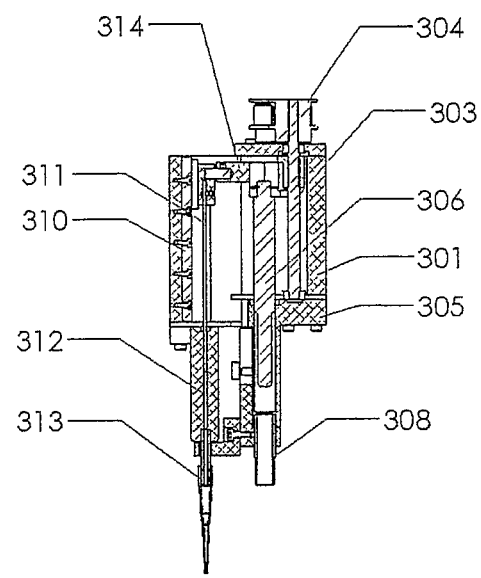
FIG. 5A is a cross section of the dispense head of FIG. 5

With reference to FIGS. 5 and 5A, the dual tip dispensing head 300 is shown with the piston 311 in the fully retracted position. Small pipette tips 313 are depicted coupled to small tip couplers for aspirating or dispensing small volumes in an automated fluid transfer system. With reference to FIG. 5, the dual tip dispensing head 300 is shown coupled to small pipette tips 313. When viewed along cross-section B-B of FIG. 5, block 314 coupled to small dispense piston 311 is shown fully retracted in frame 301 in FIG. 5A. Large piston 306 is also shown fully retracted into frame 301, with block 314 at the top of leadscrew 303.

With the small dispense pistons 311 in the retracted position, as shown in FIG. 5A, the dual tip dispensing head 300 is shown coupled with the small pipette tips 313. In this configuration, vertical linear motion of a small dispense piston 311 allows for aspiration or dispensing of fluid from pipette tips 313. Large dispense pistons 306 are also in the fully retracted position, with the large tip couplers 308 in a configuration to receive small pipette tips.

I claim:

1. An automated tool for sample transfer comprising:
   a dispense head;
   a first set of tip couplers of a first tip coupler size, said first set of tip couplers mounted on said dispense head and configured to aspirate and dispense samples;
   a second set of tip couplers of a second tip coupler size, said second set of tip couplers mounted on said dispense head parallel to said first set of tip couplers and configured to aspirate and dispense samples;
   a single drive system configured to actuate both said first set of tip couplers and said second set of tip couplers allowing each of said first set of tip couplers and said second set of tip couplers to separate and dispense samples;
   a motor coupled to said drive system allowing said single drive system to sequentially actuate said first set of tip couplers and said second set of tip couplers;
   a first ejector mechanism configured to eject tips from said first set of tip couplers, said first ejector means driven by said single drive system; and
   a second ejector mechanism configured to eject tips from said second set of tip couplers, said second ejector means driven by said single drive system;
   wherein said single drive system actuates a piston associated with each tip coupler;
   wherein said first set of tip couplers is smaller than the second set of tip couplers.

2. The automated tool of claim 1, wherein said single drive system actuates a block mechanically connected to a set of large pistons associated with large tip couplers, and a set of small pistons associated with small tip couplers.

3. The automated tool of claim 2, wherein the block is actuated by a leadscrew driven by said single drive system.

4. The automated tool of claim 1, wherein said first and second ejector means are pistons actuated by said single drive system.

* * * * *